(12) United States Patent
Stinson et al.

(10) Patent No.: US 7,780,798 B2
(45) Date of Patent: Aug. 24, 2010

(54) MEDICAL DEVICES INCLUDING HARDENED ALLOYS

(75) Inventors: Jonathan S. Stinson, Plymouth, MN (US); Matthew Cambronne, Mounds View, MN (US); Richard B. Frank, Reading, PA (US); Richard A. Gleixner, Wyomissing, PA (US); James E. Heilmann, West Lawn, PA (US)

(73) Assignees: Boston Scientific Scimed, Inc., Maple Grove, MN (US); CRS Holdings, Inc., Wilmington, DE (US)

( * ) Notice: Subject to any disclaimer, the term of this patent is extended or adjusted under 35 U.S.C. 154(b) by 535 days.

(21) Appl. No.: 11/693,498

(22) Filed: Mar. 29, 2007

(65) Prior Publication Data

US 2008/0091267 A1 Apr. 17, 2008

Related U.S. Application Data

(60) Provisional application No. 60/851,583, filed on Oct. 13, 2006.

(51) Int. Cl.
*C22C 38/40* (2006.01)
*C22C 38/44* (2006.01)
*C22C 5/04* (2006.01)
*C22C 28/00* (2006.01)

(52) U.S. Cl. ............. 148/326; 148/327; 148/419; 623/1.15; 623/924; 420/35; 420/43; 420/468; 420/584.1; 420/586.1

(58) Field of Classification Search ............. 420/35, 420/43, 466, 584.1, 586.1, 468; 148/325–327, 148/419, 430; 623/1.15, 924
See application file for complete search history.

(56) References Cited

U.S. PATENT DOCUMENTS 3,174,851 A 3/1965 Buehler et al.

(Continued)

FOREIGN PATENT DOCUMENTS

EP 1 239 464 A2 9/2002

(Continued)

OTHER PUBLICATIONS

U.S. Appl. No. 11/035,316, filed Jan. 13, 2005, Stinson et al.

(Continued)

*Primary Examiner*—Deborah Yee
(74) *Attorney, Agent, or Firm*—Fish & Richardson P.C.

(57) ABSTRACT

Medical devices, such as endoprostheses, and methods of making the devices are disclosed. The endoprostheses comprise a tubular member capable of maintaining patency of a bodily vessel. The tubular member includes a mixture of at least two compositions, where the presence of the second composition gives the mixture a greater hardness than that of the first composition alone. The first composition includes less than about 25 weight percent chromium, less than about 7 weight percent molybdenum, from about 10 to about 35 weight percent nickel, and iron. The second composition is different from the first and is present from about 0.1 weight percent to about 5 weight percent of the mixture.

20 Claims, 1 Drawing Sheet

U.S. PATENT DOCUMENTS

| | | | |
|---|---|---|---|
| 3,351,463 A | 11/1967 | Rozner et al. | |
| 3,408,178 A | 10/1968 | Myers et al. | |
| 3,753,700 A | 8/1973 | Harrison et al. | |
| 4,384,891 A * | 5/1983 | Barnabe | 420/35 |
| 4,668,290 A | 5/1987 | Wang et al. | |
| 4,958,625 A | 9/1990 | Bates et al. | |
| 5,000,912 A | 3/1991 | Bendel et al. | |
| 5,087,415 A | 2/1992 | Hemphill et al. | |
| 5,089,223 A * | 2/1992 | Hamada et al. | 420/40 |
| 5,090,419 A | 2/1992 | Palestrant | |
| 5,195,969 A | 3/1993 | Wang et al. | |
| 5,209,799 A | 5/1993 | Vigil | |
| 5,238,004 A | 8/1993 | Sahatjian et al. | |
| 5,270,086 A | 12/1993 | Hamlin | |
| 5,336,234 A | 8/1994 | Vigil et al. | |
| 5,366,504 A | 11/1994 | Andersen et al. | |
| 5,368,045 A | 11/1994 | Clement et al. | |
| 5,383,892 A | 1/1995 | Cardon et al. | |
| 5,393,488 A | 2/1995 | Rhoads et al. | |
| 5,411,613 A | 5/1995 | Rizk et al. | |
| 5,512,237 A | 4/1996 | Stigenberg | |
| 5,605,693 A | 2/1997 | Seare, Jr. | |
| 5,629,077 A | 5/1997 | Turnlund et al. | |
| 5,632,826 A | 5/1997 | Hultin-Stigenberg et al. | |
| 5,674,242 A | 10/1997 | Phan et al. | |
| 5,681,528 A | 10/1997 | Martin et al. | |
| 5,720,300 A | 2/1998 | Fagan et al. | |
| 5,759,308 A | 6/1998 | Hultin-Stigenberg et al. | |
| 5,780,807 A | 7/1998 | Saunders | |
| 5,800,511 A | 9/1998 | Mayer | |
| 5,888,201 A | 3/1999 | Stinson et al. | |
| 5,919,126 A | 7/1999 | Armini | |
| RE36,382 E * | 11/1999 | Hultin-Stigenberg | |
| 5,980,553 A | 11/1999 | Gray et al. | |
| 6,106,642 A | 8/2000 | DiCarlo et al. | |
| 6,146,404 A | 11/2000 | Kim et al. | |
| 6,171,327 B1 | 1/2001 | Daniel et al. | |
| 6,238,455 B1 | 5/2001 | Brown et al. | |
| 6,280,185 B1 * | 8/2001 | Palmer et al. | 433/8 |
| 6,287,331 B1 | 9/2001 | Heath | |
| 6,342,062 B1 | 1/2002 | Suon et al. | |
| 6,364,902 B1 | 4/2002 | Dickenson et al. | |
| 6,419,693 B1 | 7/2002 | Fariabi | |
| 6,451,052 B1 | 9/2002 | Burmeister et al. | |
| 6,485,507 B1 | 11/2002 | Walak et al. | |
| 6,508,803 B1 | 1/2003 | Horikawa et al. | |
| 6,565,599 B1 | 5/2003 | Hong et al. | |
| 6,616,689 B1 | 9/2003 | Ainsworth et al. | |
| 6,620,192 B1 | 9/2003 | Jalisi | |
| 6,629,994 B2 | 10/2003 | Gomez et al. | |
| 6,630,103 B2 | 10/2003 | Martin et al. | |
| 6,652,576 B1 | 11/2003 | Stalker | |
| 6,656,220 B1 | 12/2003 | Gomez et al. | |
| 6,676,987 B2 | 1/2004 | Zhong et al. | |
| 6,723,120 B2 | 4/2004 | Yan | |
| 6,726,712 B1 | 4/2004 | Raeder-Devens et al. | |
| 2002/0144757 A1 | 10/2002 | Craig et al. | |
| 2003/0003220 A1 | 1/2003 | Zhong et al. | |
| 2003/0018380 A1 * | 1/2003 | Craig et al. | 623/1.15 |
| 2003/0077200 A1 * | 4/2003 | Craig et al. | 420/52 |
| 2003/0185895 A1 | 10/2003 | Lanphere et al. | |
| 2004/0044397 A1 | 3/2004 | Stinson | |
| 2004/0088043 A1 | 5/2004 | Klein | |
| 2004/0143317 A1 | 7/2004 | Stinson et al. | |
| 2004/0191404 A1 | 9/2004 | Hossainy et al. | |
| 2005/0051243 A1 | 3/2005 | Forbes Jones et al. | |
| 2005/0059889 A1 | 3/2005 | Mayer | |
| 2005/0070990 A1 | 3/2005 | Stinson | |
| 2005/0089438 A1 | 4/2005 | Stinson | |
| 2005/0131522 A1 | 6/2005 | Stinson et al. | |
| 2005/0209680 A1 | 9/2005 | Gale et al. | |
| 2006/0079953 A1 | 4/2006 | Gregorich et al. | |
| 2006/0222844 A1 | 10/2006 | Stinson | |

FOREIGN PATENT DOCUMENTS

| | | |
|---|---|---|
| GB | 2 145 734 A | 4/1985 |
| WO | WO 02/078764 A1 | 10/2002 |
| WO | WO 2004/062707 A1 | 7/2004 |
| WO | 2004/108021 A2 | 12/2004 |

OTHER PUBLICATIONS

Schetky, "Shape-Memory Alloys," *Encyclopedia of Chemical Technology*, Third Edition, vol. 20, John Wiley & Sons, New York, pp. 726-736 (1982).

International Search Report received in PCT Application No. PCT/US2005/036420, mailed Feb. 16, 2006.

Jan Weber, "Medical Devices", U.S. Appl. No. 10/335,604, filed Jan. 2, 2003.

Denki Jiki Zairyo Kenkyusho, Abstract for JP Patent No. 2003 166026, Jun. 13, 2003.

Tokuriki Honten KK, Abstract for JP Patent No. 61 076634, Apr. 19, 1986.

Mitsubishi Metal Corp, Abstract for JP Patent No. 59 143032, Aug. 16, 1984.

Partial International Search received in PCT/US2004/034580, dated Apr. 26, 2005.

Authorized Officer Dina Schmid, International Search Report/Written Opinion in PCT/US2007/81126 mailed Aug. 9, 2009, 21 pages.

Authorized Officer Beate Giffo-Schmitt, International Preliminary Report on Patentability in PCT/US2007/81126 mailed Sep. 24, 2009, 21 pages.

* cited by examiner

MEDICAL DEVICES INCLUDING HARDENED ALLOYS

CROSS-REFERENCE TO RELATED APPLICATION

This application claims the benefit of the filing date of U.S. Provisional Patent Application Ser. No. 60/851,583, filed on Oct. 13, 2006, the entire contents of which are hereby incorporated by reference.

TECHNICAL FIELD

The invention relates to medical devices, such as endoprostheses (e.g., stents).

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

SUMMARY

The invention relates to medical devices, such as endoprostheses.

Generally stated, one aspect of the invention features an endoprosthesis (for example, a stent), comprising a tubular member capable of maintaining patency of a bodily vessel. The tubular member includes a mixture of at least two compositions, where the presence of the second composition gives the mixture a greater hardness than that of the first composition alone. The first composition includes less than about 25 weight percent chromium, less than about 7 weight percent molybdenum, from about 10 to about 35 weight percent nickel, and iron. The second composition is different from the first and is present from about 0.1 weight percent to about 5 weight percent of the mixture.

In some embodiments, the second composition may be present as particles, e.g., having an average width from about 10 nm to about 500 nm. The second composition may be selected from the group consisting of Ni—Ti (e.g. NiTi2, NiTi, Ni3Ti), Ni—Al (e.g. NiAl3, Ni2Al3, Ni5Al3, Ni3Al), Ni—Nb (e.g. Ni8Nb, Ni3Nb, Ni6Nb7), Fe—Nb (e.g. Fe2Nb, FeNb), Ni—Ta (e.g. Ni8Ta, Ni3Ta, Ni2Ta, NiTa, NiTa2), Fe—Ta (Fe2Ta,FeTa), Pt—Ir (PtIr), Pt—Au (e.g. PtAu3, PtAu, Pt3Au), Cr—Pt (e.g. Cr3Pt, CrPt, CrPt3), Pt—Cu (e.g. PtCu3, PtCu, Pt5Cu3, Pt3Cu), Ni—Cu (NiCu), and Fe—Cu (FeCu). The mixture may have a hardness of from about 95 Rockwell B to about 50 Rockwell C. The mixture may comprise less than about 2,000 ppm of carbon, nitrogen, and/or oxygen. The mixture may further include particles comprising a third composition different from the first and second compositions. The tubular member may be comprised substantially entirely of the mixture or less than the entire tubular member may comprise the mixture. The tubular member may comprise a band and an elongated portion extending from the band (e.g., with the band having a lower yield strength than that of the elongated portion), and either the band the elongated portion, or both, comprise the mixture. The first composition may include a 300 series stainless steel. It may also include platinum, iridium, gold, tantalum, hafnium, tungsten, palladium, rhodium, lead, and/or silver, present, for example, from about 1 to about 40 weight percent of the first composition. The tubular member may include multiple layers, at least one of which comprises the mixture. The wall thickness of at least part of the tubular member may be from about 0.0020 inch to about 0.0030 inch.

In another embodiment, a medical device (for example in the form of an endoprosthesis, a wire, a cutting element configured to be supported by a medical balloon, or an orthopedic implant), comprises a mixture having a first composition and a second composition as described above in the general aspect and in the preferred embodiments.

A third aspect of the invention generally features a method of making a medical device, by forming a second composition in a first metallic composition to provide a mixture having a hardness greater than a hardness of the first metallic composition. The mixture is then included in at least a portion of the medical device. In specific embodiments, the second composition is formed by precipitating it. The mixture may be as described above in the preferred embodiments, and the medical device may be as described above.

Embodiments may include one or more of the following advantages. The hardened stainless steels can have enhanced hardness and yield strength. The hardened stainless steels can be used to make stents with thin walls. A thin walled stent may be easily delivered through a tortuous path and may be implanted in a smaller bodily vessel. A thin wall also provides less blockage and allows more bodily fluid to flow unrestrictedly through the lumen of the stent. Wall thickness is an important factor for CT and fluoroscopic imaging. A thin-walled with relatively low radiopacity may provide an improved image that does not obscure other features. Lower radiopacity also can reduce blooming artifacts sometimes observed in images of high radiopacity implants, which obscures the area within and adjacent to the implant. Alternately, if the radiopacity of the hardened stainless steel thin wall is insufficient for fluoroscopy and CT imaging, hardened platinum enhanced radiopacity stainless steel (hardened PERSS) may be used. The hardened stainless steels can be used to make a variety of medical devices and medical components.

As used herein, an "alloy" means a substance composed of two or more metals or of a metal and a nonmetal intimately united, for example, by being fused together and dissolving in each other when molten.

Other aspects, features, and advantages will be apparent from the description of the preferred embodiments thereof and from the claims.

DETAILED DESCRIPTION

Figure 1:
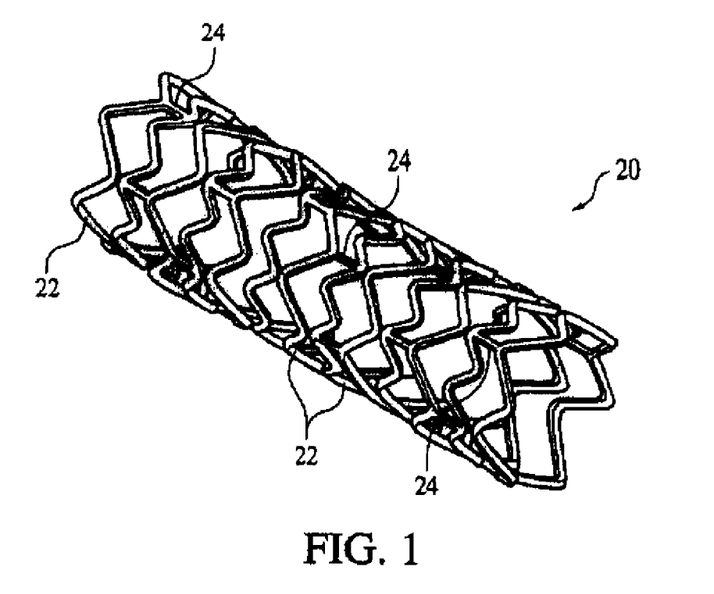
FIG. 1 is a perspective view of an embodiment of a stent.

Referring to FIG. 1, an endoprosthesis (as shown, a stent 20) has the form of a tubular member 21 capable of maintaining the patency of a bodily lumen, such as a vascular vessel. Tubular member 21 is defined by a plurality of bands 22 and a plurality of connectors 24 that extend between and connect adjacent bands. During use, bands 22 are expanded from an initial, small diameter to a larger diameter to contact stent 20 against a wall of a vessel, thereby maintaining the patency of the vessel. Connectors 24 provide stent 20 with flexibility and conformability that allow the stent to adapt to the contours of the vessel.

Figure 2:
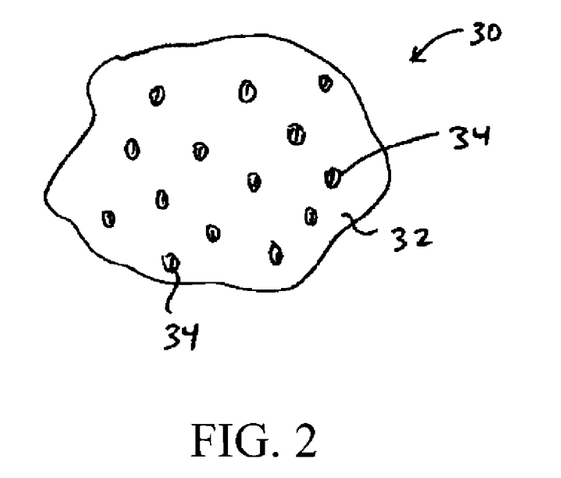
FIG. 2 is a detailed view of an embodiment of a precipitation hardened stainless steel.

Referring to FIG. 2, tubular member 21 of stent 20 includes (e.g., is formed of) a precipitation hardened stainless steel 30. As shown, precipitation hardened stainless steel 30 is mixture of a matrix 32 having a first composition, and a plurality of precipitated particles 34 embedded within the matrix and having a second composition. Precipitated particles 34 have a hardening effect so that precipitation hardened stainless steel 30 has a higher hardness than a hardness of an unmodified first composition. The enhanced hardness and strength of precipitation hardened stainless steel 30 allow stent 20 and other medical devices including the hardened stainless steel to be formed with thinner sections that would be the case for comparable devices made of the first stainless steel composition but lacking the second composition. For example, cardiovascular 3 mm diameter stent 20 including stainless steel 30 having the second composition can be formed with a thinner wall (e.g., from about 0.0010 inch to about 0.0030 inch wall thickness) relative to a stent including an unmodified first composition (e.g., from about 0.0032 inch to about 0.0044 inch wall thickness), without compromising the performance of the stent. A thinner walled stent may be more easily delivered through a tortuous path and may be implanted in a smaller bodily vessel, at least in part because a thinner wall stent has more axial flexibility than a thick wall stent. A thinner wall also provides less blockage and allows more bodily fluid to flow unrestrictedly through the lumen of stent 20. Using less material for stent 20 also reduces the amount of foreign material placed in the body when the stent is implanted.

Still referring to FIG. 2, matrix 32 includes a non-magnetic, austenitic stainless steel. In some embodiments, the stainless steel is an austenitic stainless steel, such as a 300 series stainless steel [exemplified by the following stainless steels: 310 (UNS S31000) stainless steel, PERSS (platinum enhanced radiopacity stainless steel), 314 (UNS S31400), 317 (UNS S31700), 330 (UNS N08330), Type 332 (UNS N08800), AL-6X (UNS N08366), 18-18-2 (UNS S38100), and 370 (UNS 37000)]. The stainless steels can include chromium, molybdenum, iron, and one or more other elements, such as nickel or platinum.

In particular, it is believed that chromium can enhance corrosion resistance, e.g., by increasing the pitting resistance of the stainless steel. For example, in certain stainless steels, at 12 weight percent or higher, chromium can form a thin oxide layer on the surface of a steel that enhances the resistance of the steel to corrosive attack. The degree of corrosion resistance can be a function of the chromium concentration and the concentrations of other elements in the steel. The lower limit of chromium in the stainless steels can be from about about 12, more preferably about 13, 14 or 15 weight percent and most preferably about 16, 17, 18 or 19 weight percent, and the upper limit of chromium can be about 26, more preferably about 23, 24 or 25 weight percent and most preferably 20, 21, 22, 23, 24 or 25 weight percent Alternately, 20 to 100 percent of the chromium can be replaced with platinum, because platinum contributes to the corrosion resistance of the alloy.

Molybdenum can also be added to the stainless steels to enhance the resistance of the stainless steels to corrosion, e.g., pitting and crevice corrosion. In embodiments, the stainless steels include from about 0 to about 7 weight percent of molybdenum. For example, the lower limit of molybdenum can be about 0.1 weight percent, more preferably 0.5, 1.0 or 1.5 weight percent, and most preferably 2.0, 2.5, 3.0, 3.5, 4.0 or 4.5 weight percent. The upper limit of molybdenum can be about 7 weight percent, more preferably 5.0. 5.5, 6.0 or 6.5 weight percent and most preferably 4.5. 5.0, 5.5 or 6.0 weight percent.

In certain embodiments, the stainless steels contain nickel. The stainless steels can include from about 15 to about 50 percent by weight of nickel. For example, the alloy can have less than or equal to about 50, 40 or 35 percent by weight of nickel; and/or greater than or equal to about 15, 25 or 30 percent by weight of nickel. In some embodiments, the stainless steels are substantially free of nickel, i.e., having none or less than or equal to 1% by weight of nickel (e.g., less than or equal to 0.05 or 0.03% by weight). It is believed that nickel can cause an allergic and/or cytotoxic effect in certain subjects. Therefore, by reducing the amount of nickel in the stainless steels, the occurrence of the effect(s) can be reduced (e.g., minimized or eliminated). In some embodiments, 10 to 100 percent of the nickel can be replaced with platinum, because platinum serves to stabilize the austenite phase and thereby enhance formability and reduce magnetic susceptibility like nickel.

In certain embodiments, the stainless steels contain platinum and are substantially free of nickel and can have reduced chromium and molybdenum. The stainless steels can include from about 10 to about 50 percent by weight of platinum. For example, the alloy can have less than or equal to about 50, 40 or 30 percent by weight of platinum; and/or greater than or equal to about 10, 20 or 30 percent by weight of platinum.

The stainless steels can further include one or more microalloyed elements or residual amounts of impurities elements. For example, the stainless steels can include phosphorus (e.g., 0.025 wt % maximum), silicon (e.g. 0.75 wt % maximum), sulfur (e.g., 0.010 wt % maximum), niobium (e.g., about 0.013 to 5.0 wt %), vanadium (e.g., about 0.07 wt %), titanium (e.g., 0.002 to 5.0 wt %), copper (e.g., about 0.2 to 5.0 wt %), selenium (e.g., about 0.2 wt %), tantalum (e.g., about 0.002 to 5.0 wt %), iridium (e.g., about 0.002 to 5.0 wt %), gold (e.g., about 0.002 to 5.0 wt %), and/or aluminum (e.g., about 0.009 to 5.0 wt %). Other microalloyed and residual elements are possible, which can be a function of the source of the materials.

Iron makes up the balance of the stainless steels, e.g., after accounting for the other elements in the stainless steels described above. In certain embodiments, the stainless steels include greater than 0 and less than about 60 weight percent of iron or cobalt. For example, the stainless steels can include a maximum of less than or equal to about 60, 50, 40 or 30 weight percent of iron or cobalt; and/or greater than or equal to about 0, 10, 20 or 30 weight percent of iron or cobalt.

In other embodiments, the stainless steels include one or more first elements (such as C, N, Cr, Ni, Ir, or Pt) capable of enhancing the stainless steels, e.g., one or more of their properties such as strength, hardness, and/or radiopacity. Without wishing to be bound by theory, it is believed that the first element is capable of solid solution strengthening the stainless steels by distorting the structural lattice of the stainless steels such that the lattice strains and the stainless steels strengthen. For example, the lattice parameter "a" of a first element can be larger than the lattice parameter "a" for iron (Fe=2.866). As a result, when the first element atom is incorporated into the crystallographic lattice, distortion (strain) results and the material is strengthened. In some embodiments, element X has a density equal to or greater than that of iron (7.87 g/cc). The high density of the first element can increase the radiopacity (i.e., visibility to X-rays) of the stainless steel and cobalt alloy compositions, e.g., relative to conventional commercially available iron-based stainless steel alloys (such as 316L, 304L and 410 stainless steels and MP35N and L605 cobalt alloys), which then allows certain medical devices formed from the stainless steels including the first element(s) to be monitored by X-rays. In some embodiments, the high concentration of the first element(s) can also increase the density of the stainless steels. The stainless steels including the first element(s) can have a density greater than about 9 g/cc, e.g., greater than about 9.5, 10.0, or 10.5 g/cc. The stainless steels can include a total of from about 0.01 to about 50 weight percent of one or more first elements, in any combination. The stainless steels can include greater than or equal to about 0.01, 10, 15, 20 or 25 weight percent of first element(s), and/or less than or equal to about 50, 45, 40, 35 or 30 weight percent of first element(s). Other stainless steel-based alloys are described in commonly-assigned U.S. Application Publications US-2003-0018380-A1; US-2002-0144757-A1; and US-2003-0077200-A1, all hereby incorporated by reference.

The stainless steels can be synthesized by intimately combining the components of the stainless steels. For example, to form a stainless steel including a first element, the first element (e.g., platinum) can be melted with 316L stainless steel to form a targeted stainless steel. The targeted stainless steels can also be formed by melting elemental powders in the appropriate concentrations. Melting can be performed using vacuum induction melting (VIM), vacuum arc remelting (VAR), electron beam melting (EBM), plasma melting, vacuum or inert gas plasma deposition. Solid state alloying can be performed using powder metals and hot isostatic pressing and/or cold pressing and sintering. Samples can be in the form of an ingot, a compact, or a deposit.

Still referring to FIG. 2, discrete particles 34 include (e.g., are formed of) a second composition different and distinct from the stainless steel of matrix 32 and capable of enhancing the hardness of the stainless steel. Examples of the second composition include intermetallic phases such as Ni—Ti (e.g. $NiTi_2$, NiTi, $Ni_3Ti$), Ni—Al (e.g. $NiAl_3$, $Ni_2Al_3$, $Ni_5Al_3$, $Ni_3Al$), Ni—Nb (e.g. $Ni_8Nb$, $Ni_3Nb$, $Ni_6Nb_7$), Fe—Nb (e.g. $Fe_2Nb$, FeNb), Ni—Ta (e.g. $Ni_8Ta$, $Ni_3Ta$, $Ni_2Ta$, NiTa, $NiTa_2$), Fe—Ta ($Fe_2Ta$, FeTa), Pt—Ir (PtIr), Pt—Au (e.g. $PtAu_3$, PtAu, $Pt_3Au$), Cr—Pt (e.g. $Cr_3Pt$, CrPt, $CrPt_3$), Pt—Cu (e.g. $PtCu_3$, PtCu, $Pt_5Cu_3$, $Pt_3Cu$), Ni—Cu (NiCu), Pt—Ti, Pt—Al, and Fe—Cu (FeCu). In some embodiments, particles 34 have globular shapes, spherical shapes, and/or oval shapes wherein the longest axis of the shape is less than 5 times the length of the shortest axis of the shape. The size of particles 34 can range from about 10 nm to about 500 nm in width or diameter. The width or diameter can be greater than or equal to about 10 nm, 50 nm, 100 nm, 150 am, 200 nm, or 250 nm; and/or less than or equal to about 500 nm, 450 nm, 400 nm, 350 nm or 300 nm. The concentration of particles 34 in hardened stainless steel 30 can range from about 0.1% to about 20% by weight, preferably at least 10%. The volume percentage of particles 34 in hardened stainless steel 30 can be greater than or equal to about 1; and/or less than or equal to about 30 percent by volume. Particles 34 can be generally homogeneously distributed throughout the entirety of matrix 32, or selected portion(s) of the matrix can include the particles (e.g., homogeneously) while other portion(s) of the matrix can be substantially free (e.g., less than 0.05% by weight) of the particles.

In some embodiments, hardened stainless steel 30 includes low amounts of phases that can be detrimental to the properties of the hardened stainless steel. For example, hardened stainless steel 30 can include less than about 2,000 ppm (e.g., less than about 1,500 ppm, 1,000 ppm, 500 ppm, or 100 ppm) of one or more carbon, nitrogen, and/or oxygen, which can harden and strengthen stainless steel matrix 32 but also reduce the ductility and corrosion resistance of the matrix, for example, by reacting with chromium.

Hardened stainless steel 30 can be characterized using microscopic methods and/or mechanical methods. As indicated above, particles 34 form as one or more phases distinct from stainless steel austenite matrix phase 32, and as a result, the particles can be detected (e.g., mapped) using metallography techniques, such as scanning electron microscopy (SEM), auger electron microscopy (AES) and transmission electron microscopy (TEM). The compositions of particles 34 and matrix 32 can be determined by techniques such as energy dispersive spectroscopy (EDS) X-ray analysis. Mechanically, hardened stainless steel 30 can have higher hardness, yield strength, and/or Young's modulus than those of the stainless steel austenite matrix 32. For example, stainless steel austenite matrix 32 can have a hardness of about 20 to about 95 Rockwell hardness B, while hardened stainless steel 30 can have a hardness of about 30 to about 50 Rockwell hardness C. The yield strength of hardened stainless steel 30 can range from about 65 ksi to about 150 ksi (e.g., greater than or equal to about 65 ksi, 75 ksi, 85 ksi, 95 ksi, 105 ksi or 115 ksi; and/or less than or equal to about 105 ksi, 95 ksi, 85 ksi, or 75 ksi). The ultimate tensile strength of hardened stainless steel 30 can range from about 100 ksi to about 200 ksi (e.g., greater than or equal to about 100 ksi, 105 ksi, 120 ksi, or 150; and/or less than or equal to about 200 ksi, 195 ksi, 180 ksi, or 165 ksi). The Young's modulus of hardened stainless steel 30 can range from about 27 msi to about 34 msi (e.g., greater than or equal to about 27 msi, 28 msi, or 29 msi; and/or less than or equal to about 34 msi, 33 msi, or 32 msi). The tensile elongation of hardened stainless steel 30 can range from about 10 percent to about 50 percent (e.g., greater than or equal to about 10%, 15%, or 20%; and/or less than or equal to about 50%, 45%, or 40%). Young's modulus, yield strength, and elongation are measured in accordance with ASTM E8.

As illustrated by the examples below, stent 20 can be formed by making a precipitation hardenable alloy composition, forming the precipitation hardenable alloy composition into a tubing, forming the tubing into a pre-stent, and precipitation hardening the pre-stent into stent 20.

A precipitation hardenable alloy composition can be made by melting together the constituents (elemental and/or alloy constituents) of the composition. For example, the nickel concentration of 15-50 weight percent or 20-50 weight percent of the first element (e.g., Pt or Co) and iron, chromium, and less than 5 weight percent of one or more elements (e.g., Ti, Al, Nb, Ta, Au, Ir, and/or Cu) capable of forming desired particles can be combined to form a formulation. The formulation can be melted using, for example, vacuum induction melting (VIM), electroslag remelting (ESR), AOD, and/or vacuum arc remelting (VAR), to form an ingot. The ingot can be hot worked (e.g., by hot forging and/or extrusion) to convert the as-cast microstructure to a wrought microstructure, and to form a billet. The billet can be hot rolled to form a rod suitable to manufacture a tubing. Preferably the ingot is given a homogenization heat treatment either before or after the hot working step.

In other embodiments, a billet of a precipitation hardenable alloy composition is made using powder metallurgy in which alloying is performed with elemental or alloy powders in the solid state. The billet can be hot rolled to form a rod suitable to manufacture a tubing.

The formation of the precipitation hardenable alloy composition can be performed under a vacuum or an inert atmosphere to reduce the formation of materials (such as carbide, nitrides and carbonitrides) that can be detrimental to the final hardened stainless steel. Alternatively or additionally, a scavenger material (such as calcium or potassium) can be added to the formulation and subsequently removed. The alloy can also be treated with a small addition of magnesium, cerium, lanthanum, or other rare earth metal. Preferably the cerium, lanthanum, or other rare earth metal are introduced into the alloy by the addition of mischmetal.

The rod is solution heat treated to dissolve any precipitates and thereby enhance material formability. The solutionized rod can be drawn (e.g., by cold or warm mandrel and floating plug drawing) to form a tubing. In some embodiments, the hollow tubing can be drawn through a series of dies with progressively smaller circular openings to plastically deform the tubing to a targeted size and shape. The plastic deformation strain can harden the tubing (and increases its yield strength) and elongate the grains along the longitudinal axis of the tubing. The deformed tubing can be heat treated (e.g., annealed above the grain recrystallization and precipitation temperature and/or hot isostatically pressed) to transform the elongated grain structure into an initial grain structure, e.g., one including equiaxed grains. Small or fine grains can be formed by heating the tubing close to the recrystallization temperature for a short time. Large or coarse grains can be formed by heating the tubing at higher temperatures and/or for longer times to promote grain growth. Alternatively or additionally, between drawing steps, the tubing can be annealed as necessary to maintain material formability during tubing manufacture.

Next, bands 22 and connectors 24 of stent 20 are formed, for example, by cutting the tubing, to form a pre-stent. Selected portions of the tubing can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, is flowed through the lumen of the tubing. The carrier can prevent dross formed on one portion of the tube from re-depositing on another portion, and/or reduce formation of recast material on the tubing. Other methods of removing portions of the tubing can be used, such as mechanical machining (e.g., micro-machining), electrical discharge machining (EDM), and photoetching (e.g., acid photoetching).

In some embodiments, after bands 22 and connectors 24 are formed, areas of the pre-stent affected by the cutting operation above can be removed. For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing).

The pre-stent can then be finished. The pre-stent can be finished, for example, by electropolishing to a smooth finish. Because the pre-stent can be formed to near-net size, relatively little of the unfinished stent need to be removed to finish the pre-stent. As a result, further processing (which can damage the pre-stent) and costly materials can be reduced. In some embodiments, about 0.0001 inch of the pre-stent material can be removed by chemical milling and/or electropolishing to yield a stent.

The pre-stent can be formed into stent 20 by heat treating the pre-stent to precipitate the desired particles. For example, the pre-stent can be precipitation hardened by solution heat treating at about 1800 to about 2200° F. for 2 minutes to 120 minutes to create a solid solution of an austenite phase, and subsequently heat treating at about 1000 to about 1500° F. for about 10 minutes to about 30 hours to cause strengthening precipitates to form. In some embodiments, the pre-stent is heat treated under different conditions (e.g., different temperatures and/or duration) to precipitate particles of different compositions, which may require different precipitation conditions. Heat treating under different conditions can also be used to form particles of different sizes. Particles (1 nm to 500 nm) can increase Young's modulus, yield strength, and fatigue strength. Large particles (e.g., 100 nm to 500 nm) can especially increase yield strength, and small particles (e.g., 1 nm to 99 nm) can especially increase fatigue strength.

In other embodiments, the strengthening precipitates can be formed before bands 22 and connectors 24 are formed, or before the pre-stent is finished. After the precipitates are formed, bands 22 and connectors 24 can be formed, or finishing can be performed, as described above.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 20 can be balloon-expandable, self-expandable, or a combination of both (e.g., U.S. Pat. No. 5,366,504).

In use, stent 20 can be used, e.g., delivered and expanded, using a catheter delivery system, such as a balloon catheter system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

While a number of embodiments have been described above, the invention is not so limited.

Stent 20 can be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002, hereby incorporated by reference. The therapeutic agents, drugs, or pharmaceutically active compounds can include, for example, anti-thrombogenic agents, antioxidants, anti-inflammatory agents, anesthetic agents, anti-coagulants, and antibiotics.

In some embodiments, a stent can be formed by fabricating a wire including a hardenable stainless steel or hardened stainless steel 30, and knitting and/or weaving the wire into a tubular member.

While stent 20 is shown above as being formed wholly of hardened stainless steel 30, in other embodiments, the hardened stainless steel forms one or more selected portions of the medical device. For example, stent 20 can include multiple layers in which one or more layers include hardened stainless steel 30, and one or more layers do not include hardened stainless steel 30. The layer(s) that does not include hardened stainless steel 30 can include one or more of the biocompatible materials, such as stainless steel, titanium, tantalum, platinum, iridium, or a shape memory material (e.g., nickel-titanium alloy). The layering of hardened stainless steel 30 provides yet another way to tailor and tune the properties of the medical device. Stents including multiple layers are described, for example, in published patent application US2004-0044397, and Heath, U.S. Pat. No. 6,287,331, both of which are hereby incorporated by reference.

In some embodiments, bands 22 and connectors 24 also have different amounts of hardening enhancement. For example, connectors 24 can have a higher hardness, and as a result, the connectors have a higher yield strength than the yield strength of bands 22. The high yield strength of connectors 24 allows them to have small cross-sectional sizes, which allow them to easily deform so that stent 20 can conform well to a vessel that is not straight. The yield strength and the section size are balanced to allow connectors 24 to easily deform while remaining resistant to fracture. In comparison, the low yield strength of bands 22 reduces elastic recoil when stent 20 is crimped to a delivery system and during in vivo expansion. The yield strength and the section size of bands 22 are balanced to provide good resistance to radial compression and to control elastic recoil.

Without wishing to be bound by theory, it is believed that stent 20 can experience relatively high levels of stress during use. For example, stent 20 can be bent as it tracks through a tortuous vessel during delivery, as it is expanded, and/or when it is placed in a curved vessel. After implantation, stent 20 can also experience stress from movement caused by a beating heart or by the subject's breathing. The stress that exceeds the yield strength of the material can strain the relatively narrow connectors 24 and fracture the connectors. A fractured connector can provide surfaces that disrupt blood flow and/or provide sites on which blood can aggregate and undesirably lead to blood clotting or thrombosis in the vessel. By enhancing the mechanical properties of connectors 24 (i.e., increasing the yield strength), the connectors can elastically tolerate the stress without leading to excessive straining that can lead to fracture, while still being easily deformable. At the same time, bands 22 are able to have good radial strength to support the vessel.

As used herein, a band 22 refers to a portion of a stent that extends circumferentially about the stent. The band can extend completely about the circumference of a stent, for example, such that the ends of the band are joined, or the band can extend partially about the circumference. The band can extend substantially linearly or nonlinearly, for example, in an undulating pattern or a zigzag pattern as shown in FIG. 1. In some embodiments, bands 22 are connected together by integrally formed connectors that extend between and transversely to the bands.

As used herein, a connector 24 refers to a portion of a stent that extends from a band of the stent, for example, from a first band to an adjacent second band along the length of the stent. The connector can include one strut or a plurality of struts. The connector can extend linearly (e.g., parallel to the longitudinal axis of the stent) or nonlinearly, for example, in an undulating patter or zigzag pattern. Connectors 24 include one or more curved portions, examples of which are described in U.S. Pat. Nos. 6,656,220; 6,629,994; and 6,616,689.

Bands 22 and connectors 24 having different amounts of hardening can be made by selective masking. For example, a removable shield is first placed on bands 22 and connectors 24 over portions that are to be exposed during heat treatment. The shield can be, for example, an adhesive-backed tape; a dissolvable material (such as a carbon steel that can be dissolved by immersion in an acid such as nitric acid, which can also remove certain recast material formed during manufacturing); or a material (such as gallium metal) that can be melted or sublimed during heat treatment. The shield can include a ceramic and/or a glass that can be removed by heating the tube and allowing differential thermal expansion to separate the shield from the tube. Alternatively or in addition, the shield can be removed mechanically, such as by grinding.

Next, a mask is applied over bands 22 and connectors 24 to serve as an insulative thermal barrier. Examples of materials for the mask include ceramics (such as titanium nitride, titanium carbide, and silicon carbide), including oxides (such as aluminum oxide, zirconium oxide, and magnesium oxide). The mask can be applied by slurry dipping, spraying, powder coating, physical vapor deposition, sputtering, and/or chemical vapor deposition. The shield is then removed to expose the previously shielded portions of bands 22 and connectors 24. Masking bands 22 and connectors 24 allow the bands and the connectors to be heat treated differently. Masking also allows selected small areas of the unfinished stent to be locally and thoroughly heated without substantial heat loss because the open structure of the unfinished stent can radiate heat.

After the unfinished stent is masked, the unfinished stent is heat treated to precipitate the particles. For example, the unfinished stent can be heated, for example, under vacuum or under a controlled (e.g., inert) atmosphere, in a furnace, in an induction coil, or under a heat lamp. For example, bands 22 can be more masked than connectors 24. As a result, when connectors 24 and bands 22 are heated under the same conditions, the connectors experience more heating and precipitation. In some embodiments, alternatively or additionally to covering different percentages of surface areas of bands 22 and connectors 24, different thicknesses of the mask can be deposited to effect different precipitation. For example, the mask on bands 22 can be thicker than the mask on connectors 24 to provide more insulation and therefore less heating.

Alternatively or additionally to heating as above, exposed portions of bands 22 or connectors 24 can be locally heated so that the heat treated areas are precisely targeted. For example, exposed portions can be addressed with a laser, an electron beam, or other focal heating sources, such that the heat is conducted from the exposed portions to the bulk of the tube. In some embodiments of local heating, bands 22 can be less masked than connectors 24 to dissipate heat.

In some embodiments, bands 22 and connectors 24 are not masked prior to heat treatment. Bands 22 and connectors 24 can be heat treated differently, for example, by lasing the connectors for longer times and/or with more energy to produce precipitation, compared to lasing the bands. In embodiments in which bands 22 are substantially free of hardened stainless steel 30, only the connectors are heat treated to effect precipitation.

The hardened stainless steels described herein can be used to form other medical devices or components of medical devices. For example, the hardened stainless steels can be used to form wires (e.g., used to reinforce a guide catheter), cutting elements configured to be supported by a medical balloon, metal staples and wires used for wound closure, and an orthopedic implant, such as hip stems, screws, pins, plates and knee trays.

The following examples are illustrative and not intended to be limiting.

EXAMPLE 1

PERSS (Platinum Enhanced Radiopacity Stainless Steel)[1] alloy utilizes platinum as a means of enhancing radiopacity and solid solution strengthening relative to 316L stainless steel which is commonly material used to make intravascular balloon expandable stents. A considerable amount of platinum is added to 316L alloy to cause in an increase in annealed material yield strength from about 40 ksi to about 60 ksi (with 30 weight percent platinum). The price of the platinum added to the alloy is significant (about $900 per troy ounce). An embodiment of the invention is to add platinum only for radiopacity enhancement and to utilize the precipitation hardening to achieve yield strength enhancement.

[1] Stainless Steels for Medical and Surgical Applications, Editors: Gary L. Winters and Michael J. Nutt, STP 1438, ASTM International, 2003, Development of a Platinum-Enhanced Radiopaque Stainless Steel (PERSS), pages 28-38.

A PERSS alloy with 20 weight percent platinum was made to be precipitation hardenable by adding nickel, titanium and aluminum to the composition. Melting of the precipitation hardenable 20 PERSS (PH 20 PERSS) alloy (20Pt-30.5Ni-17.4Cr-2.3Ti-0.9Al-0.03Mo-Bal Fe) was performed by vacuum induction melting the elemental charge materials and casting a 12-pound rectangular ingot.

The ingot was heated to red hot and forged into a bar; 1.75 inch×1.75 inch square cross-section by 14 inches long. After forging, the PH 20 PERSS bar was given a homogenization heat treatment to reduce material segregation remaining from solidification and then processed to 0.725 inch round bar. Precipitation hardening heat treatments (aging treatments) were performed on samples of the round bar. Hardness tests were performed on the heat treated samples. All of this processing and testing was performed by Carpenter Specialty Alloys (Reading, Pa.).

TABLE 1

Hardness test results for PH 20 PERSS bar samples. The HRC hardness scale is for materials with hardness values higher than can be measured with the HRB hardness scale.

| Condition: | Hardness Scale: | Hardness Test Result: |
| --- | --- | --- |
| As-Forged | HRC | 43 |
| Solution Annealed at 2000° F. for 1 hour, oil quench | HRB | 94 |
| Aged at 1350° F. for 24 hours, air cooled | HRC | 47 |
| Solutioned and aged at 2000° F. +1350° F. | HRC | 42 |

The hardness results indicated that the PH 20 PERSS samples were significantly hardened (strength is directly proportional to hardness) by the aging treatments.

The bar of PH 20 PERSS was machined to a round cross-section and sent to Minitubes (Grenoble, France) for conversion to tubing.

Upon receipt, Minitubes performed an initial characterization of the bars and determined that the PH 20 PERSS bar had an ASTM E112 average grain size number (G) of 2 to 3 and had a hardness of 33 to 36 HRC (Rockwell C-scale). For comparison, a standard (non-PH) 20 PERSS alloy bar (20Pt-18Cr-9Ni-2.6Mo-bal Fe) had an ASTM E112 average grain size number of 2 or less and had a lower hardness than the PH 20 PERSS; 82 to 86 HRB (Rockwell B-scale). The bars were gun drilled to produce hollow rods for tube drawing.

Before attempting the first tube manufacturing draw pass through the die, the hardness of the PH 20 PERSS would need to be reduced from the 30's HRC to 90's HRB to prevent cracking during drawing. Carpenter performed a one hour anneal at 2000° F. followed by a fast air cool. Following the annealing treatment, Carpenter measured the hardness of the rod to be 93 HRB.

Minitubes successfully used fixed mandrel drawing practice to convert the PH 20 PERSS hollow rod to a tube with 0.64 inch OD and 0.44 inch ID. The tube could then be solution annealed and tube drawing continued to fabricate stent tubing for the manufacture of stents. The solution annealed stent tubing or laser machined and electropolished stents could then be subjected to precipitation hardening heat treatment.

EXAMPLE 2

A small PH 20 PERSS ingot was produced by arc melting elemental charge materials procured from Goodfellow and Alfa Asear. The arc melter (Materials Research Furnaces, Inc. ABJ-900) was laboratory-scale equipment that is used to make prototype alloy samples. The alloy formulation was 20Pt-30.5Ni-17.4Cr-2.3Ti-0.9Al-0.03Mo-Bal Fe. The charge materials used are listed below.

(1) Nickel Wire
  Diameter: 1 mm
  Length: 10 m/reel
  Purity: 99.98%
  Temper: Hard
  Goodfellow P/N: NI005171
  Goodfellow order code: 508-872-55

-continued

| | |
|---|---|
| (2) | Chromium Lump<br>Lump Size: 10 mm<br>Weight: 50 g<br>Purity: 99.95%<br>Goodfellow P/N: CR006115<br>Goodfellow order code: 324-549-96 |
| (3) | Aluminum Wire<br>Diameter: 1 mm<br>Length: 10 m/reel<br>Purity: 99.95%<br>Goodfellow P/N: AL005183<br>Goodfellow order code: 990-089-72 |
| (4) | Iron Lump<br>Lump Size: 10 mm<br>Weight: 100 g<br>Purity: 99.95%<br>Goodfellow P/N: FE006100<br>Goodfellow order code: 052-688-21 |
| (5) | Molybdenum Wire<br>Diameter: 1.0 mm<br>Weight: 201 g<br>Purity: 99.95%<br>Goodfellow P/N: MO005160<br>Goodfellow order code: 520-155-75 |
| (6) | Titanium Rod<br>Diameter: 5 mm<br>Weight: 892 g<br>Purity: 99.6+%<br>Goodfellow P/N: TI007920<br>Goodfellow order code: 968-344-93 |
| (7) | Platinum Grain<br>Weight: 115 g<br>Purity: 99.9%<br>Alfa Aesar Stock No.: 73356<br>Alfa Aesar UN: B27N13 |

The ingot was machined to produce a 0.2" thick rectangular rolling blank with flat and parallel sides. The blank was successfully cold rolled into 0.020" thick strip.

PH 20 PERSS strip samples for tensile testing.

One of the PH 20 PERSS strips was solution annealed at 2000° F. for 30 minutes and aged at and 1350 F for 4 hours to cause precipitation hardening. The other PH 20 PERSS strip was solution annealed at 2000° F. for 30 minutes followed by a fast air cool. The strips were tensile tested in accordance with ASTM E8. The tensile results were compared to standard 20 PERSS strip test results. The PH 20 PERSS strip that had been solution annealed and aged had a significantly higher yield strength than the solution annealed PH 20 PERSS and standard 20 PERSS materials. This demonstrates how much strength enhancement can ultimately be achieved, but a heat treatment that provided less yield strength enhancement and higher elongation would be preferred; e.g., 80-90 ksi YS and >20% elongation.

| Material | Heat Treatment | Yield Strength (KSI) | Ultimate Strength (KSI) | Elongation (%) |
|---|---|---|---|---|
| PH 20 PERSS | Solution Anneal | 55 | 114 | 50 |
| PH 20 PERSS | Solution Anneal + Age | 134 | 175 | 12 |
| Std. 20 PERSS | Solution Anneal | 49 | 102 | 48 |

EXAMPLE 3

A PERSS alloy with 20 weight percent platinum could be made to be precipitation hardenable by adding nickel, titanium and aluminum to the composition. Melting of the precipitation hardenable 20 PERSS (PH 20 PERSS) alloy (20Pt-30.5Ni-17.4Cr-2.3Ti-0.9Al-0.03Mo-Bal Fe) could be performed by vacuum induction melting the elemental charge materials and casting a 7-pound rectangular ingot.

The ingot could be heated to red hot and forged into a bar; 1.75 inch×1.75 inch square cross-section by 14 inches long. After forging, the PH 20 PERSS bar could be given a homogenization heat treatment to reduce material segregation remaining from solidification.

The bar of PH 20 PERSS could be machined to a round cross-section and sent to Minitubes (Grenoble, France) for conversion to tubing. Minitubes had the bar gun drilled to produce a hollow rod.

Minitubes could use fixed mandrel and floating plug mandrel drawing practice to convert the hollow rod to a tube with 0.08 inch OD and 0.004 inch wall thickness. The tube could be solution annealed at 2000° F. for 20 minutes. Stents could be laser machined from the tube. An Excimer laser could then be used to locally (i.e., selectively) precipitation harden strut undulation peaks (hinge points for stent balloon expansion) by cyclically heating the target area. By pulsing the laser on the target area, heat conduction to adjacent areas would be minimized, thereby concentrating the hardening effect to the targeted area. The treated stents would then be electropolished to produce finished dimensions and surface roughness. Upon expansion, the stents would have higher hoop compression resistance, because of the strengthened strut peaks. Stent performance would be improved, because the hardened stents could better resist compression than annealed 316L stainless steel stents. If a stent is compressed after implantation, it can result in an obstruction to blood flow through the stented artery.

All publications, references, applications, and patents referred to herein are incorporated by reference in their entirety.

Other embodiments are within the claims.

What is claimed is:

1. An endoprosthesis, comprising a tubular member capable of maintaining patency of a bodily vessel, the tubular member comprising a mixture comprising a matrix having a first composition and a plurality of particles embedded within the matrix, the plurality of particles having a second composition, the first composition comprising less than about 25 weight percent chromium, less than about 7 weight percent molybdenum, from about 10 to about 35 weight percent nickel, iron, and platinum, the second composition being different from the first composition and being present from about 0.1 weight percent to about 5 weight percent of the mixture, wherein the second composition is selected from the group consisting of Pt—Ir, Pt—Au, Cr—Pt, Pt—Cu, Pt—Ti, and Pt—Al, wherein the mixture has a hardness greater than a hardness of the first composition.

2. The endoprosthesis of claim 1, wherein the particles have an average width from about 10 nm to about 500 nm.

3. The endoprosthesis of claim 1, wherein the second composition is selected from the group Pt—Ir, $PtAu_3$, PtAu, $Pt_3Au$, $Cr_3Pt$, CrPt, $CrPt_3$, $PtCu_3$, PtCu, $Pt_5Cu_3$, and $Pt_3Cu$.

4. The endoprosthesis of claim 1, wherein the mixture has a hardness of from about 95 Rockwell B to about 50 Rockwell C.

5. The endoprosthesis of claim 1, wherein the mixture comprises less than about 2,000 ppm of carbon, nitrogen, and/or oxygen.

6. The endoprosthesis of claim 1, wherein the mixture further comprises particles comprising a third composition different from the first and second compositions.

7. The endoprosthesis of claim 1, wherein the tubular member consists of the mixture.

8. The endoprosthesis of claim 1, wherein less than the entire tubular member comprises the mixture.

9. The endoprosthesis of claim 1, wherein the tubular member comprises a band, and an elongated portion extending from the band, at least one of the band and the elongated portion comprising the mixture.

10. The endoprosthesis of claim 9, wherein the band has a yield strength lower than a yield strength of the elongated portion.

11. The endoprosthesis of claim 1, wherein the first composition comprises from about 1 to about 40 weight percent of platinum.

12. The endoprosthesis of claim 1, wherein the endoprosthesis comprises a stent.

13. The endoprosthesis of claim 1, wherein the tubular member comprises multiple layers, at least one of the layers comprising the mixture.

14. The endoprosthesis of claim 1, wherein the tubular member comprises a wall thickness from about 0.0020 inch to about 0.0030 inch.

15. A medical device comprising a precipitation hardenable alloy having a composition comprising in weight percent:

|  | wt. % |
| --- | --- |
| Chromium | 10-25; |
| Nickel | 10-35; |
| Molybdenum | 0-7; |
| Platinum | 10-50; |

One or more elements selected from the group consisting of:

| | |
| --- | --- |
| Copper | about 0.2-5.0, |
| Niobium | about 0.013-5.0, |
| Titanium | about 0.002-5.0, |
| Aluminum | about 0.009-5.0, |
| Tantalum | about 0-0.2, |
| Iridium | about 0.002-5.0, and |
| Gold | about 0.002-5.0; | and the balance being iron and usual impurities, wherein matrix is embedded with a plurality of particles in a weight percent range from about 0.1% to about 5% and selected from the group consisting of Pt—Ir, Pt—Au, Cr—Pt, Pt—Cu, Pt—Ti, and Pt—Al, and wherein the particles have a hardness greater than hardness of the matrix.

16. The medical device of claim 15, wherein the precipitation hardenable stainless steel contains at least about 15% platinum and not more than about 20% chromium.

17. The medical device of claim 15 wherein the precipitation hardenable stainless steel contains at least about 1.5% titanium and at least about 0.5% aluminum.

18. The medical device of claim 15 wherein the precipitation hardenable stainless steel contains at least about 0.5% molybdenum.

19. The medical device of claim 15 wherein the precipitation hardenable stainless steel contains at least about 15% nickel.

20. The medical device of claim 15 wherein the precipitation hardenable stainless steel contains about 0.025% max. phosphorus, about 0.75% max. silicon, about 0.010% max. sulfur, about 0.07% max. vanadium, and about 0.2% max selenium.

* * * * *

UNITED STATES PATENT AND TRADEMARK OFFICE
CERTIFICATE OF CORRECTION

| | | |
|---|---|---|
| PATENT NO. | : 7,780,798 B2 | Page 1 of 1 |
| APPLICATION NO. | : 11/693498 | |
| DATED | : August 24, 2010 | |
| INVENTOR(S) | : Jonathan S. Stinson et al. | |

It is certified that error appears in the above-identified patent and that said Letters Patent is hereby corrected as shown below:

Title Page, Column 2, (57) Abstract, Line 1: delete "endoprostheses" and insert --endoprosthesis--.

Title Page, Column 2, (57) Abstract, Line 2: delete "endoprostheses" and insert --endoprosthesis--.

Column 16, Claim 20, Line 33: delete "max" and insert --max.--.

Signed and Sealed this
Fourth Day of January, 2011

David J. Kappos
*Director of the United States Patent and Trademark Office*